United States Patent [19]
Temin et al.

[11] Patent Number: 5,554,524
[45] Date of Patent: Sep. 10, 1996

[54] MORE COMPLEX TYPE RETROVIRUSES HAVING MIXED TYPE LTR, AND USES THEREOF

[75] Inventors: Howard M. Temin, Madison; Kathleen A. Boris-Lawrie, Middleton, both of Wis.

[73] Assignee: Wisconsin Alumni Research Foundation, Madison, Wis.

[21] Appl. No.: 264,115

[22] Filed: Jun. 22, 1994

Related U.S. Application Data

[63] Continuation of Ser. No. 21,622, Feb. 17, 1993, abandoned.

[51] Int. Cl.$^6$ .............................. C12N 7/00; C12N 7/01; C12N 15/00; C12N 15/09
[52] U.S. Cl. .................................. 435/235.1; 435/320.1; 536/23.72; 536/24.1; 424/199.1
[58] Field of Search ................................ 435/172.3, 91.4, 435/69.1, 320.1; 424/202.1, 199.1, 207.1, 298.1, 93.21, 813; 536/23.72

[56] References Cited

U.S. PATENT DOCUMENTS

| | | |
|---|---|---|
| 4,650,764 | 3/1987 | Temin et al. . |
| 4,980,289 | 12/1990 | Temin et al. . |
| 5,124,263 | 6/1992 | Temin et al. . |

FOREIGN PATENT DOCUMENTS

| | | |
|---|---|---|
| WO9102805 | 3/1991 | WIPO . |
| 9119803 | 12/1991 | WIPO . |

OTHER PUBLICATIONS

Brenner, M., 1994 Immunomethods 5:204–210.
Leiden, J., 1995 New Engl. J. Med. 333:871–873.
Mulligan, R., 1993 Science 260:926–932.
Norley, S. et al. Immunobiol. "Vaccination Against HIV" 184: 193–207 (1992).
Temin, H. M. 1990. "Safety considerations in somatic gene therapy of human disease with retrovirus vectors". Hum. Gene. Ther. 1:111–123.
Ellis, R. W. 1988. "New technologies for making vaccines". In: Vaccines, Plotkin & Mortimer Eds. W. B. Saunders Co. pp. 568–575.
J. Dougherty et al., 168 Mol. Cel. Biol. 4387–4395 (1986).
J. Dougherty et al., 63 J. Virol. 3209–3212 (1898).
H. Temin et al., The Retroviridae, vol. 1, p. 1–17 (1992).
T. Matthews et al., Sci. Am. 120–127 (Oct., 1988).
D. Montefiori et al., 64 J. Virol. 5223–5225 (1990).
M. Marthas et al., 64 J. Virol. 3694–3700 (1990).
P. Marx et al., 60 J. Virol. 431–435 (1986).
M. Seiki et al., 80 P.N.A.S. USA 3618–3622 (1983).
D. Derse et al., 64 J. Virol. 401–405 (1990).
N. Sagata et al., 80 P.N.A.S. USA 677–681 (1985).
R. Weiss et al., RNA Tumor Viruses, pp. 766–785, appendix (2d Edition 1985) (Cold Spring Harbor).
J. Salk et al., 83 Annals NY Acad. Sci. 609–636 (1960).
A. Allison et al., 95 J. Immun. Met. 157–168 (1986).
M. Daniel et al., 258 Science 1938–1941 (1992).
R. Desrosiers, 8 AIDS Res. Human Retrovir. 411–421 (1992).
I. Ghattas et al., 11 Mol. Cel. Biol. 5848–5859 (1991).
F. Moolten et al., 82 J. Nat. Can. Inst. 297–300 (1990).
C. Mullen et al., 89 P.N.A.S. USA 33–37 (1992).
P. Southern et al., 1 J. Mol. Appl. Gene. 327–341 (1982).
C. Yanisch–Perrson et al., 33 Gene 103–119 (1985).
A. Miller, 1 Humn. Gen. Ther. 5–14 (1990).

*Primary Examiner*—Robert D. Budens
*Assistant Examiner*—Jeffrey S. Parkin
*Attorney, Agent, or Firm*—Quarles & Brady

[57] ABSTRACT

Chimeric retroviral vectors were constructed containing the long terminal repeats (LTRs) from a simple retrovirus (e.g. spleen necrosis virus (SNV); murine leukemia virus (MLV)) devoid of the integration site (att) and more complex retroviral (e.g. bovine leukemia virus (BLV); human immunodeficiency virus (HIV)) cis-acting regulatory sequences (e.g. att; primer binding site (PBS); encapsidation site (E), and polypurine tract (ppt)) and coding regions. Cells transfected with these constructs produce replication competent retrovirus particles. These retroviral particles provide a source of viral antigens that can be employed in both diagnostic assays and as immunogens for the production of high-titer specific antisera.

12 Claims, 2 Drawing Sheets

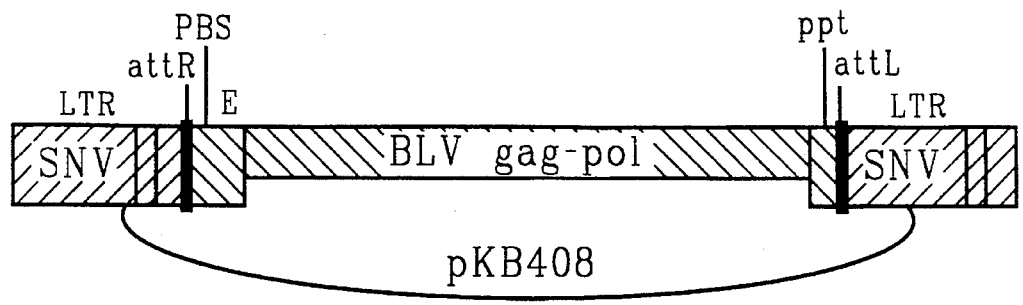
FIG. 4
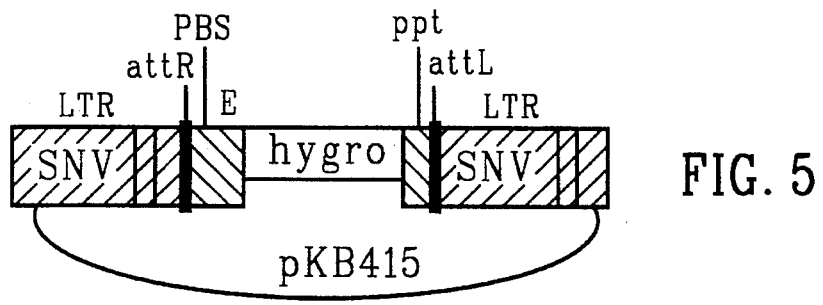
FIG. 5
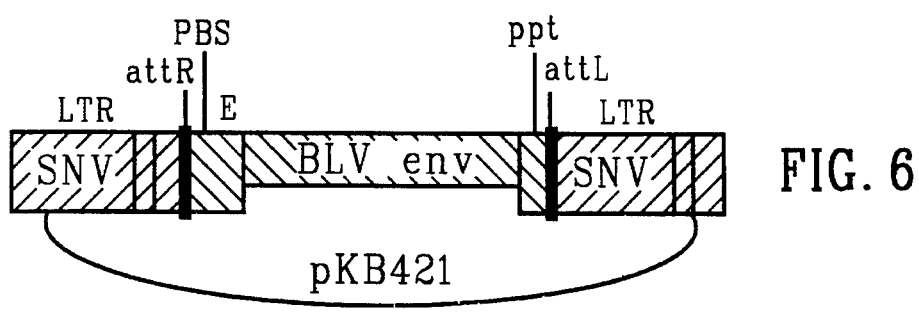
FIG. 6
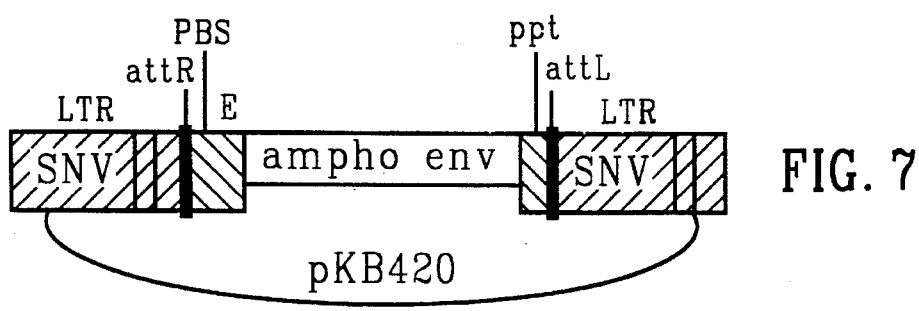
FIG. 7
FIG. 8

5,554,524

MORE COMPLEX TYPE RETROVIRUSES HAVING MIXED TYPE LTR, AND USES THEREOF

This invention was made with the United States Government support awarded by the National Institute of Health (NIH), Grants Nos. CA07175 and CA22443. The United States Government has certain rights in this invention.

This is a file wrapper continuation of application Ser. No. 08/021,622, filed Feb. 17, 1993, now abandoned.

FIELD OF THE INVENTION

The field of the present invention is recombinant retroviruses that are useful to produce antigens.

BACKGROUND OF THE INVENTION

Retroviruses are a type of RNA virus that replicate through a DNA intermediate. FIG. 1 illustrates examples of two types of retroviruses—simpler "S Type" and more complex "MC Type". All retroviruses have gag, pol, and env genes. For some retroviruses (e.g. spleen necrosis virus; murine leukemia virus) only these genes are needed for viral replication. Such viruses are called "simpler" or "S Type" retroviruses. (See e.g. U.S. Pat. Nos. 4,650,764; 4,980,289; and 5,124,263. The disclosure of these patents and of all other publications referred to herein are incorporated by reference as if fully set forth herein.) Other retroviruses, called "more complex" or "MC Type" retroviruses, need additional genes for replication. Among the more complex retroviruses are human immunodeficiency virus (HIV), human spumaretrovirus, human T-lymphotropic virus type I (HTLV-I), and bovine leukemia virus (BLV).

The additional genes of the more complex retroviruses are thought essential for replication of the natural virus. In this regard, the additional genes in complex retroviruses are known to code for proteins that act on transcription, splicing, and polyadenylation. See generally H. Temin, et. al., *The Retroviridae*, v. 1, New York, 1, 5 (1992).

The genomes of both simpler and more complex retroviruses have some common features. Both types of RNA viruses replicate through a DNA intermediate. Therefore, both simpler and more complex retroviruses have DNA and RNA genomes. The viral DNA genomes for both types of retroviruses are bounded by long terminal repeats (LTRs). These LTRs contain enhancer, promoter, usually 3' RNA processing sequences, and integration sequences ("att").

Simpler and more complex retroviruses have different infection cycles. Temin (*The Retroviridae*, Supra pp. 1, 6–7) describes these two different infection cycles. The primary difference relates to the involvement of regulatory proteins in the more complex retrovirus cycle.

In nature, disease caused by simpler retroviruses are found in various non-mammalian hosts, but not primates or ungulates. However, diseases caused by more complex retroviruses are prevalent in ungulates and primates (especially humans).

For many more complex retroviruses there is, as yet, no safe and effective vaccine against the disease caused by the virus. Reasons for this are believed to be that certain more complex regulatory retroviral proteins interfere with the immune response and/or that retroviruses tend to mutate too rapidly in vivo for the body to provide a long-term immune response. Therefore, there is a need to find a way to produce representative spectrums of varied more complex retroviral Gag, Pol, and Env antigens, albeit without producing other disease-causing complex retroviral proteins.

SUMMARY OF THE INVENTION

In one aspect, the invention provides a recombinant retroviral DNA sequence that has an S Type retroviral long terminal repeat except for att and encodes MC Type retroviral proteins and att, pbs, E, and ppt (integration sequence, primer binding site, encapsidation and polypurine tract, respectively).

Preferably, the sequence encodes a replication competent virus and MC Type retroviral proteins encoded by the DNA sequence are selected from the group consisting of Env, Gag, and Pol protein.

In another aspect, the invention provides a recombinant retrovirus. The retrovirus comprises an RNA sequence that has S Type retroviral termini except for att, and a RNA sequence encoding a MC Type retroviral protein and att, pbs, E, and ppt. Again, the virus is preferably replication competent.

In yet another aspect, the invention provides a method of producing antigens in a host cell. One introduces the above virus into a mammalian (e.g. primate) cell and allows the virus to replicate and produce viral proteins.

In still another aspect, the invention provides a method of producing antibodies within a host. One infects the host and allows the virus to replicate such that at least one MC Type retroviral protein is produced. If desired, antibodies will then form against the MC Type retrovirus protein.

An object of the present invention is therefore to produce antigens for certain, but not all, MC Type retroviral proteins.

Another object of the present invention is to produce a replication competent virus that has S Type retroviral long terminal repeats except for att and encodes MC Type retroviral proteins.

Another object is to provide such a virus such that it will raise an antigenic response when injected into a host.

It is another feature of the present invention to provide a virus of the above type wherein the virus will mutate similarly to the way the naturally occurring MC Type retrovirus would when in a host.

Other features, objects and advantages of the present invention will become apparent after review of the specification, claims, and drawings.

DESCRIPTION OF THE DRAWINGS

FIG. 4 depicts a schematic diagram of the vector pKB408;

FIG. 5 depicts a schematic diagram of the vector pKB415;

FIG. 6 depicts a schematic diagram of the vector pKB421;

FIG. 7 depicts a schematic diagram of the vector pKB420; and

FIG. 8 is a legend describing the nature of the sequences in FIGS. 4–7.

DESCRIPTION OF THE PREFERRED EMBODIMENTS

1. In General

The main principle behind the present invention is the ability of primates and ungulates to respond to infection by live simpler retroviruses with a protective response. In this regard, live simpler retroviruses do not cause a disease state in primates and ungulates. Our discovery is that more complex retroviruses could have almost all of their LTRs removed, be provided with almost all of simpler type retroviral LTRs, have sequences coding certain other more complex retroviral proteins be deleted, and the new recombinant virus would still be replication competent. This is especially surprising as more complex natural retroviruses require more complex type regulatory retroviral proteins to replicate.

We have thus constructed an S Type retrovirus that expressed the Gag, Pol, and Env proteins of a representative MC Type retrovirus. Preferably, this virus is replication competent and thus is suitable to induce an antigenic response against not only the original virus, but also against mutated forms of the virus. Because the construct would not have certain required more complex retroviral proteins, it would not cause a MC type virus disease state even if the live virus were used to raise antibodies in a host.

If desired, one could reduce the risks of working with a live virus by first letting the virus go through several infection cycles in vitro and then inactivating the virus. One could then use the inactivated virus as an antigen.

Figure 1:
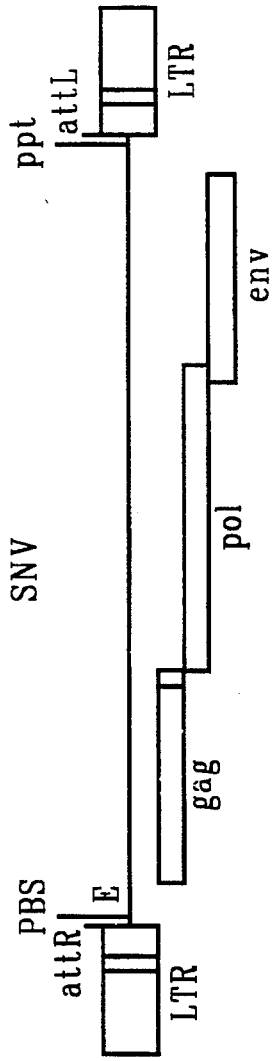
FIG. 1 depicts a schematic diagram of the prior art "Simpler" SNV retrovirus.

We first worked with bovine leukemia virus (BLV) as a representative more complex retrovirus (see FIG. 1). BLV has tax and rex genes, in addition to gag, pol, and env genes. The products of the tax and rex genes act on sequences in the BLV long terminal repeats (LTRs). We constructed chimeric retrovirus DNA vectors from BLV and the simpler retrovirus spleen necrosis virus (SNV). We substituted simpler retrovirus cis-acting control sequences from SNV for most of the more complex retrovirus control sequences found in BLV and deleted some sequences coding for regulatory genes (tax/rex).

As described below, we replaced all of the BLV LTRs except for the terminal attachment sequences (attR and attL), about 10 base pairs on each end, with the analogous sequences from the LTR of SNV and deleted the BLV tax and rex genes. For convenience, and to reduce recombination risk, the gag-pol and env genes were expressed on separate chimeric vectors. However, these three genes could be expressed on a single vector. The BLV genes were expressed by the chimeric LTR, and our experiments showed that the resulting chimeric BLV/SNV virus was replication competent.

A similar "simpler HIV" could be constructed by taking the HIV-1 gag, pol, and env genes (a source of these genes being the cell line HUT78 (HIV-1$_{SF2}$) found in the N.I.H. AIDS Research And Reference Reagent Program Catalog #279, January 1992, National Institutes Of Health, Publication No. 2-1536). and replacing the cis-acting LTR control sequences acted on by the Gag and Pol proteins of HIV-1 with the transcription and polyadenylation sequences from SNV or another simpler retrovirus. In particular, as for BLV, this construct could be created by substituting simpler retrovirus LTR sequences for all of the HIV-1 LTR sequences except for the att sequences. Such a substitution would also delete the HIV TAR sequence. If desired, more HIV-1 proteins can be left in (e.g. vpu, vif) to facilitate replication, albeit at least one HIV-1 protein should be deleted (e.g., tat).

2. Materials And Methods.

Figure 2:
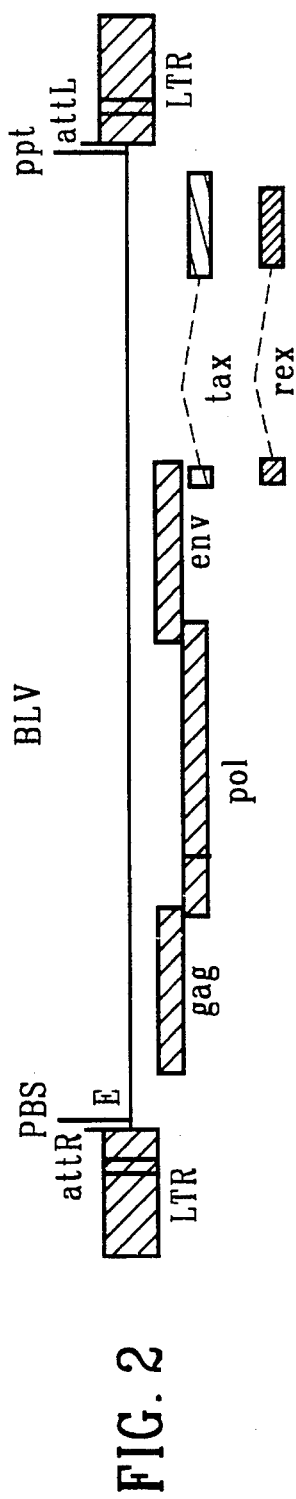
FIG. 2 depicts a schematic diagram of the prior art "More Complex" BLV retrovirus.
Figure 3:
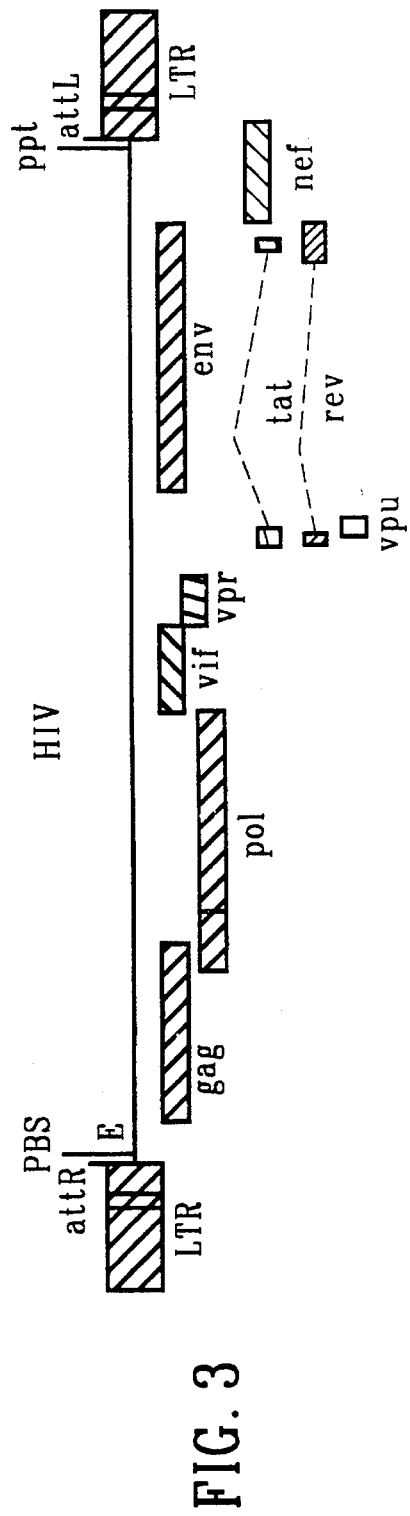
FIG. 3 depicts a schematic diagram of the prior art "More Complex" HIV retrovirus.

Vector Construction. FIG. 2 is a schematic diagram of four retroviral vectors that we created. These vectors were constructed using polymerase chain reaction (PCR) cloning, oligonucleotide cloning, and restriction fragment cloning.

To construct a parental plasmid, pKB404, the SNV LTRs were amplified using PCR. pJD220SVHy, as described in U.S. Pat. No. 4,980,289, and as noted therein as deposited as ATCC 67397, was used as template DNA. The PCR primers were complementary to pJD214Hy sequences 15 to 626. See J. Dougherty, et al., 168 Mol. Cell. Bio. 4387–4395 (1986) and contained unique terminal NarI and EcoRI or HindIII and AflIII restriction sites. The sequences of the NarI and EcoRI primers are described below at SEQ ID NOs:1 and 2. The HindIII and AflIII primers are described at SEQ ID NOs: 3 and 4. The PCR products were cloned at the opposite ends of the multiple cloning site of pUC19 (Yanisch-Perron et al., 33 Gene 103–119 (1985)) to construct pKB404.

In similar fashion other simpler retrovirus LTRs may be used instead of the SNV LTRs. To obtain such other simpler retroviral sequences, one would obtain a preparation of another simpler retrovirus, amplify the LTR sequences using PCR techniques, and insert the sequences into a suitable cloning vector, such as pUC19. In all cases, it is preferred that the simpler LTR include the promoter and enhancer, but the art sequence of the more complex virus should preferably be used.

For example, with the murine leukemia virus, the sequence of the LTR is reported at R. Weiss et al., RNA Tumor Viruses, p 766–785, appendix (2nd Edition, 1985) (Cold Spring Harbor). One could amplify and isolate this sequence, as we describe for SNV, and incorporate these LTRs into a vector such as pUC19.

BLV sequences were inserted in the parental plasmid, pKB404. The 3' cis sequences of BLV are within a 36 base pair (bp) sequence of BLV (polypurine tract, ppt, and attachment sequence left, attL; BLV sequences 8170 to 8206, See N. Sagata et al., PNAS USA 82:677–681, 1985). A pair of complementary oligonucleotides were synthesized that contained these sequences and unique, terminal SphI and HindIII sites. The oligonucleotides were treated with kinase, annealed, and inserted into the SphI and HindIII sites of pKB404 to make pKB406.

The 5' cis sequences of BLV are within an 111 bp sequence of BLV (BLV sequences 517 to 626; Sagata et al., 1985). These sequences were amplified by PCR from pBLVSV$_2$neo (D. Derse, et al. J. Virol 64:401–405 (1990)) using primers containing unique EcoRI and KpnI sites. The sequence of the primers we used is described at SEQ ID Nos: 5 and 6. The amplified product was inserted into the EcoRI and KpnI sites of pKB406 to make pKB414.

In order to create a selectable vector, the hygromycin resistance gene of pJD214Hy (see also pJD220SVHy as described in U.S. Pat. No. 4,980,289) can be isolated as a SmaI to BamHI fragment and ligated into pKB414 to make pKB415 (FIG. 2). Thus, pKB415 contains the sequences required for reverse transcription, integration, and packaging of vector virus RNA and can be selected using hygromycin.

The vector pKB408 (FIG. 2) was designed to express the BLV Gag and Pol proteins. To construct pKB408, oligonucleotides were synthesized that contained the BLV 5' cis sequences between nucleotides 517 to 551 and unique, terminal EcoRI and KpnI sites. See Sagata et al., supra. The oligonucleotides were treated with kinase, annealed, and cloned into pKB406 to make pKB407. The gag-pol fragment from pBLVSV$_2$neo was isolated as a BclI fragment (sequences 552 to 5250) and inserted into the BamHI site of pKB407 to make pKB408 (FIG. 2).

To construct an envelope co-virus vector (pKB421 or the alternative pKB420), the env genes of BLV (or in the alternative, amphotropic MLV) were amplified using PCR and cloned. The BLV env gene can, for example, be amplified from pBLVSV$_2$neo (Derse et al. supra) using primers containing unique KpnI and XbaI sites. The sequence of the primers is described at SEQ ID NOs: 7 and 8. The PCR product was digested with KpnI and XbaI and ligated to pKB414 to make pKB421 (FIG. 2).

If a different env is desired, the amphotropic MLV env gene can be subcloned from pJD1 (Doughtery et al., J. Virol., 63:3209–3212 (1989)) on an XbaI fragment and ligated at the XbaI site of pKB414 to make pKB420 (FIG. 2).

Vectors pKB408, pKB421, and pKB415 have been deposited in host D17 dog cells with the American Type Culture Collection, Rockville, Md., U.S.A. Accession No. ATCC 11259 on Feb. 2, 1993 under the terms of the Budapest Treaty. Samples from the deposits will be made available in accordance with U.S. and applicable foreign patent law requirements. Deposit of these materials does not imply that a license for their use has been granted.

In sum, we constructed chimeric retroviral vectors. We used most of the LTRs from the simpler retrovirus. The terminal regions of the BLV LTR that are required for provirus integration were maintained (attR and attL), as well as other non-LTR BLV cis sequences required for reverse transcription, and packaging, (PBS, E, and ppt). However, at least one more complex retroviral protein-encoding DNA sequence (and in our case the coding sequences for the regulatory genes, tax and rex,) can be deleted.

3. Protocol To Generate Viruses From The Vectors.

Our experimental protocol to replicate virus is summarized below:

| | |
|---|---|
| Step 1: | Transfect D17 (A.T.C.C. CRL 8468) cells with pKB408 and pKB415.<br>Select hygromycin resistant cell clones.<br>⇓<br>Infect or transfect with BLV or env expression plasmid.<br>⇓<br>Expand cells and harvest vector virus.<br>⇓ |
| Step 2: | Infect fresh D17 cells with step 1 virus.<br>Select hygromycin resistant clones.<br>⇓<br>Transfect with env expression plasmid and pSV2neo marker<br>Select G418 resistant cells.<br>⇓<br>Expand step 2 cells and harvest vector virus.<br>⇓ |
| Step 3: | Infect fresh D17 cells with step 2 vector virus.<br>Select hygromycin resistant step 3 cells. |

Retroviral vector plasmids pKB408 and pKB415 were cotransfected into dog osteosarcoma cells, D17, and hygromycin resistant (Hyg®) clones were selected and designated step 1 clones. D17 cells are permissive for replication of both SNV and BLV. The presence of each plasmid in the step 1 cells was confirmed by PCR analysis.

To allow chimeric vector virus to be transferred to step 2 cells, viral envelope protein was expressed in the step 1 clones that contained both pKB415 and pKB408, and transfer of vector viruses was assayed. Expression plasmids encoding the amphotropic MLV env (pJD1; Dougherty et al., supra) or SNV env (pPR101; Dougherty et al., supra) and the selectable plasmid, $pSV_2neo$ (described at P. Southern et al. J. Mol. Appl. Gen. 1:327–341.(1982)) were cotransfected into the step 1 cells, and colonies resistant to the neomycin analog, G418, were selected. The BLV env was introduced to step 1 cells by infection with supernatant media from FLK BLV cells. The supernatant media from the transfected or infected cells was used to infect D17 target cells which were selected for Hyg®. Transfer of Hyg® vector virus was detected in the presence of the BLV env, the A-MLV env, or the SNV env. This result indicated that the hyg® gene and the BLV genes are expressed by the chimeric vectors.

Hyg® step 2 clones were screened by PCR analysis for clones that contained both KB415 and KB408 proviruses. Two of these step 2 clones were cotransfected with pJDl and $pSV_2neo$, and G418® cells were selected. To transfer step 2 vector virus, supernatant medium was used to infect D17 cells, and the target cells were selected for Hyg®. Six step 3 cells were selected that contained the Hyg® vector virus (KB415). Therefore, the chimeric virus can replicate.

4. Replication-Competent Co-Viruses.

The experimental protocol in which the env co-viruses were introduced to provide successive transfer of the chimeric vector viruses is schematically described below:

| | |
|---|---|
| Step 1: | Transfect D17 cells with pKB408 and pKB415.<br>Select hygromycin resistant cell clones.<br>⇓<br>Transfect with env co-virus and pSV2neo<br>Select G418 resistant cells.<br>⇓<br>Expand cells and harvest vector virus.<br>⇓ |
| Step 2: | Infect fresh D17 cells with step 1 virus.<br>Select hygromycin resistant cells.<br>⇓<br>Harvest vector virus from pool of cells.<br>⇓ |
| Step 3: | Infect fresh D17 cells with vector virus pool.<br>Screen pool for proviruses<br>by reverse transcriptase assay and PCR analysis. |

Step 1 clones were cotransfected with the co-virus vectors, pKB421 or pKB420, and $pSV_2neo$, and G418 resistant colonies were selected. Supernatant medium from the step 1 pool was used to infect D17 target cells. These step 2 cells were screened for the vector viruses by reverse transcriptase assay and selection of Hyg® colonies. Reverse transcriptase activity was detected from the step 2 pool, and Hyg® colonies were observed. These results indicated that the co-viruses can replicate as a replication-competent chimeric retrovirus.

Supernatant medium from a pool of step 2 cells was used to infect fresh D17 cells. These step 3 cells were screened for the chimeric proviruses by reverse transcriptase assays, selection for Hyg® colonies, and PCR analysis. The results indicated that the chimeric vector viruses were successively transferred to the step 3 cells.

These experiments demonstrated that the chimeric vector virus is replication-competent, can be obtained from the deposited cell line, and can be successively transferred by the chimeric co-viruses.

5. Use Of Other More Complex Retroviral Sequences.

Other more complex retroviral sequences may be used in the present invention to create constructs containing simpler retroviral LTRs flanking more complex retroviral sequences. The DNA sequences (and functions of those sequences) for a wide variety of complex retroviruses are known. See e.g. G. Myers, *Human Retroviruses And AIDS* (Theoretical Biology And Biophysics) (1990) (HIV-1) and M. Seiki, et al, 80 P.N.A.S. U.S.A. 3618–3622 (1983) (HTLV-I).

For example, one could attach simpler retrovirus SNV LTR sequences to internal HIV att, Pbs, E, ppt and coding sequences. It is necessary that sufficient HIV sequences be present to produce a replication competent system, but at least one HIV protein should be deleted (e.g. Tat of HIV) (sequences numbers 5839–6049 and 8381–8474), and the LTRs deleted (sequence numbers 61–611 and 9121–9737) by the above techniques and then inserted in pKB408 in place of the BLV sequence. If desired, still other HIV-1 sequences could be removed (e.g. rev, vif, vpr, and/or nef).

6. Chimeric Retroviruses As An Antigen Provider.

The chimeric BLV retroviral vectors encode antigens Gag, Pol, and Env. These are antigens of interest to research per se. However, the antigens could also be used in vivo to raise an antibody response.

Efficiency of antibody response in a primate (for HIV- 1) may be tested in a chimpanzee and SIV-macaque model system. See R. Desrosiers, AIDS Res. Hu. Retrovir., 8:411–21 (1992) and M. D. Daniel, et al., Science 258:1938–41 (1992). If desired, a killed vaccine (which can be made from the virus) could be used.

In the alternative, the live construct could be partially crippled (attenuated) by mutating promoter and enhancer sequences or adding a suicide gene expressed from a picornaviral internal ribosome entry site. F. L. Moolten, et al., J. Natl. Canc. Inst., 82:297–305 (1990); C. A. Mullen, et al., Proc. Natl. Acad. Sci. USA, 89:33–7 (1992); and I. R. Ghattas, et al., Mol. Cell. Biol., 11:5848–59 (1991).

To prepare a live chimeric virus for use in raising an antibody response (e.g. for use as a potential vaccine), supernatant medium from infected cells (KB408 and KB421) could be harvested, filtered (0.4 um pore size) to remove cells, and concentrated by ultracentrifugation at 35,000 RPM for 2 hours. The virus preparation would preferably be administered intravenously (Marthas et al., J. Virol. 64:3694 (1990)). It is expected that concentrations of chimeric virus in the range of 0.5 to 5.0 ml will be injected under a subcutaneous or intramuscular protocol until an antibody response is raised in a mammal.

To determine an effective amount of the recombinant retrovirus or retroviral protein for use in a vaccine, one would typically create preparations with increasing amounts of retrovirus proteins. One would then develop a protocol to determine when a sufficient amount of preparation had been administered to a test animal to raise an antibody response and/or provide disease resistance.

Similar determinations could be made with any other more complex retrovirus used.

The following is a preferred method to develop an inactivated viral vaccine. Virus is harvested from the supernatant medium of cells infected with chimeric virus (such as KB408 and KB421). The supernatant medium is centrifuged, preferably at 10,000 RPM, to remove cells and concentrated by ultracentrifugation, preferably at 35,000 RPM for 2 hrs. To inactivate the chimeric virus, the virions are resuspended in formalin (0.8%) and incubated at 4° C. for 24 hr. See Salk et al., Ann. NY Acad. Sci. 83:609 (1960); Marx et al. J. Virol. 60:431 (1986); and Montefiori. et al., J. Virol. 64:5223 (1990).

To ensure that the chimeric virus is inactivated, an aliquot of the formalin-treated virus could be washed free of formalin and used to infect D17 target cells. The recovery of chimeric virus could be monitored by reverse transcriptase assay or by a vector rescue assay. See Miller, Hum. Gene Therapy 1:5 (1990). To assist the immunogenic effect of the formalin treated-vaccine, the vaccine could be combined with an adjuvant, such as threonyl muramyl dipeptide Allison and Byars, J. Immuno. Methods 95:157 (1986). The preparation is preferably administered intramuscularly (Montefiori et al., supra, J. Virol. 64:5223 (1990)).

It is expected that when sufficient virus or viral protein is used the antibody response will be such that the host will be immunized. Thus, the viruses, attenuated or killed sources thereof, or the proteins they express, could act as vaccines for BLV, HIV-1 and other more complex retrovirus. In this regard, humans, other primates, and ungulates all have an antibody and a protective immune responses to S Type retroviruses.

Moreover, and most importantly, because the viruses are missing more complex retroviral proteins critical to the disease, no retroviral disease like those caused by the original more complex retrovirus results from exposure to the recombinant retroviruses.

In any event, regardless of the utility as a vaccine or antibody production inducer, there is significant value in being able to obtain a supply of more complex retroviral Env, Gag, and/or Pol that is produced in large quantity by a retroviral replication competent vector in the absence of other more complex retroviral proteins. This is especially so when the vector has gone through multiple infection cycles (and thus possibly mutation). For example, the present invention is useful in raising focused antigens that can be used via the Kohler/Milstein (or other techniques) to raise monoclonal antibodies. They can also be used as antigens in ELISA tests.

The invention is not to be limited to the above preferred embodiments. Rather, attention should be directed to the claims to judge the full scope of the invention.

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: Oligonucleotide ( x i ) SEQUENCE DESCRIPTION: SEQ ID NO:1:

TTTTTTTTT GGCGCCGTGC TGGCTCGCTA ACTGC 35

( 2 ) INFORMATION FOR SEQ ID NO:2:

( i ) SEQUENCE CHARACTERISTICS:
( A ) LENGTH: 36 base pairs
( B ) TYPE: nucleic acid (C) STRANDEDNESS: single
        (D) TOPOLOGY: linear (ii) MOLECULE TYPE: Oligonucleotide (xi) SEQUENCE DESCRIPTION: SEQ ID NO:2:

TTTTTTTTA GAATTCGTAC TACGGATTCA GTCCGG    36

(2) INFORMATION FOR SEQ ID NO:3:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:3:

TTTTTTTTT AAGCTTGTGC TGGCTCGCTA ACTGC    35

(2) INFORMATION FOR SEQ ID NO:4:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:4:

TTTTTTTTA ACATGTGTAC TACGGATTCA GTCCGG    36

(2) INFORMATION FOR SEQ ID NO:5:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:5:

AAAAAAAAG GTACCATATA ATTTGAAGGA GAGACCC    37

(2) INFORMATION FOR SEQ ID NO:6:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:6:

AAAAAAAAG AATTCGAGAC CGGCAAACAA TTGGGG    36

(2) INFORMATION FOR SEQ ID NO:7:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Oligonucleotide (x i) SEQUENCE DESCRIPTION: SEQ ID NO:7:

AAAAAAAAG GTACCCTGGC GTTTGCTGAA AGCC                                    3 4

(2) INFORMATION FOR SEQ ID NO:8:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (i i) MOLECULE TYPE: Oligonucleotide (x i) SEQUENCE DESCRIPTION: SEQ ID NO:8:

AAAAAAAAT CTAGATCAAG GGCAGGGTCG GAGG                                    3 4

We claim:

1. A plurality of recombinant retroviral expression vectors capable of expressing replication competent retroviral virus particles, each expression vector comprising:
    an S Type retroviral long terminal repeat and DNA encoding MC Type retroviral protein, wherein each expression vector encodes a MC Type att, pbs, E, and ppt, and wherein the encoded MC Type retroviral protein is bovine leukemia viral Env, Gag, or Pol protein;
    wherein all three of said bovine leukemia viral Env, Gag and Pol cannot be expressed from any single such expression vector, but all can be expressed collectively by said plurality of expression vectors.

2. The expression vectors of claim 1, wherein the expression vectors do not encode an S Type att.

3. Replication competent recombinant retrovirus particles, each particle comprising:
    an RNA sequence having S Type retroviral long termini, encoding a MC Type att, pbs, E and ppt, and encoding bovine leukemia viral Env, Gag or Pol proteins;
    wherein all three of said bovine leukemia viral Env, Gag, and Pol proteins cannot be expressed from any single such RNA sequence, but all can be expressed collectively by said plurality of RNA sequences.

4. A plurality of recombinant retroviral expression vectors capable of expressing replication competent retroviral virus particles, each expression vector comprising:
    an S Type retroviral long terminal repeat and DNA encoding MC Type retroviral protein, wherein each expression vector encodes a MC Type att, pbs, E, and ppt, and wherein the encoded MC Type retroviral protein is human immunodeficiency viral Env, Gag, or Pol protein;
    wherein all three of said human immunodeficiency viral Env, Gag and Pol cannot be expressed from any single such expression vector, but all can be expressed collectively by said plurality of expression vectors.

5. The expression vectors of claim 4, wherein the expression vectors do not encode an S Type att.

6. Replication competent recombinant retrovirus particles, each particle comprising:
    an RNA sequence having S Type retroviral long termini, encoding a MC Type att, pbs, E and ppt, and encoding human immunodeficiency viral Env, Gag or Pol proteins;
    wherein all three of said human immunodeficiency viral Env, Gag, and Pol cannot be expressed from any single such RNA sequence, but all such proteins can be expressed collectively by said plurality of RNA sequences.

7. A recombinant retroviral expression vector capable of expressing a replication competent retroviral virus particle, comprising:
    an S Type retroviral long terminal repeat and DNA encoding MC Type retroviral protein, wherein the expression vector encodes a MC Type att, pbs, E, and ppt, and wherein the encoded MC Type retroviral protein is bovine leukemia viral Env, Gag, and Pol protein.

8. The expression vector of claim 7, wherein the vector does not encode an S Type att.

9. A replication competent recombinant retrovirus particle, comprising:
    an RNA sequence having S Type retroviral long termini, encoding a MC Type att, pbs, E and ppt, and encoding bovine leukemia viral Env, Gag and Pol proteins.

10. A replication competent recombinant retroviral expression vector capable of expressing a retroviral virus particle, comprising:
    an S Type retroviral long terminal repeat and DNA encoding MC Type retroviral protein, wherein the expression vector encodes a MC Type att, pbs, E, and ppt, and wherein the encoded MC Type retroviral protein is human immunodeficiency viral Env, Gag, and Pol protein.

11. The expression vector of claim 10, wherein the expression vector does not encode an S Type att.

12. A replication competent recombinant retrovirus particle, comprising:
    a recombinant RNA sequence having S Type retroviral long termini, encoding a MC Type att, pbs, E and ppt, and encoding human immunodeficiency viral Env, Gag and Pol proteins.

* * * * *